United States Patent [19]

Taniguchi

[11] Patent Number: 4,983,923

[45] Date of Patent: Jan. 8, 1991

[54] FRICTIONAL ELECTROSTATIC VOLTAGE MEASURING EQUIPMENT

[75] Inventor: Motoji Taniguchi, Osaka, Japan

[73] Assignees: Kanebo Ltd., Tokyo; Kanebo Engineering Ltd., Osaka, both of Japan

[21] Appl. No.: 377,607

[22] Filed: Jul. 10, 1989

[30] Foreign Application Priority Data

Jul. 13, 1988 [JP] Japan .................................. 63-175995

[51] Int. Cl.$^5$ ............................................ G01N 27/60
[52] U.S. Cl. ..................................................... 324/454
[58] Field of Search ................. 324/452, 454, 457, 458

[56] References Cited

U.S. PATENT DOCUMENTS 4,724,392 2/1988 Bandara et al. ...................... 324/454

FOREIGN PATENT DOCUMENTS

| 62-11303 | 3/1987 | Japan . |
| 62-38656 | 8/1987 | Japan . |
| 62-267658 | 11/1987 | Japan . |
| 62-287148 | 12/1987 | Japan . |
| 436299 | 12/1974 | U.S.S.R. ............................. 324/454 |
| 600429 | 3/1978 | U.S.S.R. ............................. 324/454 |

OTHER PUBLICATIONS

IEEE Transactions on Industry and Applications, vol. IA-13, No. 3, May/Jun. 1977, pp. 223-226.

Primary Examiner—Reinhard J. Eisenzopf
Assistant Examiner—Maura K. Regan
Attorney, Agent, or Firm—Stevens, Davis, Miller & Mosher

[57] ABSTRACT

Frictional electrostatic voltage measuring equipment for measuring the frictional electrostatic voltage characteristics and the discharge characteristics of a sheet-form sample such as textile and film, the sheet-form sample being held by a sample plate in a stretched condition. A sample table for holding detachably the sample plate is provided reciprocably on a body base; a rubbing unit comprising a rubbing pad and its driving unit, a pedestal and an electrostatic voltage sensor are provided. The sample held by the sample plate on the sample table is rubbed by the rubbing pad with the sample supported by the pedestal from its back, the sample table being allowed to move to a measuring position after the completion of rubbing. At this point, the electrostatic voltage of the sample is detected by the electrostatic voltage sensor, and the detecting signal is processed by a data processor.

7 Claims, 8 Drawing Sheets

FRICTIONAL ELECTROSTATIC VOLTAGE MEASURING EQUIPMENT

BACKGROUND OF THE INVENTION

The present invention relates to a frictional electrostatic voltage measuring equipment for measuring the frictional electrostatic voltage characteristics and the discharge characteristics of a sheet-form sample of textile such as cloth, knitted goods and non-woven fabric, and of a sample such as paper, leather and resin film.

Recently, there has been a rapidly increased demand for a static-control type fiber capable of inhibiting the electrification due to friction and the like and used for applications, for example, the static-control clothes used for semiconductor manufacturing process and the carpets treated so as to protect human body from receiving electrostatic shock. In a situation where many companies have developed various raw materials in response to gradually more sophisticated demand for static control properties, there has been also an increased needs for equipment for evaluating static control properties.

Although equipment for measuring frictional electrostatic voltage characteristics in accordance with the JIS L 1094 have been commercially available, they are insufficient with respect to accuracy and repeatability. Therefore, to develop equipment capable of accurately and simply measuring electrostatic properties has been regarded as extremely important.

As a method for improving the accuracy and repeatability in measuring electrostatic voltage, the following methods have been proposed.

The method disclosed in Japanese Pat. published No. 38656/1987 is a method with which the electrostatic voltage of a sheet-form sample is measured by rubbing the sample with mechanical reciprocating motion or rotating motion using a brush with bristles.

The method disclosed in Japanese Pat. published No. 11303/1987 is a method with which a sheet-form sample with its back supported by a supporting object is urged on its front with a rubbing object to effect rubbing and then allowed to move to the side of a detector along straight line or curve so that the electrostatic voltage of the sample may be measured. The supporting of the sample from its back when rubbed allows the accuracy and repeatability of measurement to be improved.

The method disclosed in Japanese Pat. laid open No. 267658/1987 is a method with which the electrostatic voltage of a sample is measured with a detector facing the sample by moving a supporting object to separate from the sample after or simultaneously with the end of rubbing. The separation of the supporting object from the sample allows the effect on measurement due to the electrification of the supporting object to be eliminated, and the measuring accuracy to be improved.

The method disclosed in Japanese Pat. laid open No. 287148/1987 is a method in which a textile sample with its back supported by a supporting object is rubbed on its surface by a rubbing object, moved while adhering to said supporting object simultaneously with or after the end of rubbing, faced to an electrostatic detector, separated from the said supporting object simultaneously with or after the completion of movement, and measured for electrostatic voltage by the electrostatic detector facing the sample.

In these methods, all samples are supported by a supporting object. However, some problems still remain unsolved in that attaching and detaching of a sample to and from the supporting object is difficult to perform, and sequential measurement of many samples requires much labor.

SUMMARY OF THE INVENTION

The object of the present invention is to provide frictional electrostatic voltage measuring equipment which can accurately and simply measure electrostatic properties, in particular can easily attach and detach a sample, and can efficiently measure many samples.

The frictional electrostatic voltage measuring equipment according to the present invention is constructed such that a sample table reciprocally movable between a measuring position and a rubbing position is located on a body base and such that a sample plate holding a sheet-form sample in stretched condition is detachably inserted into said sample plate. A pedestal supporting a sample from its back and a rubbing unit are provided on said rubbing position of the body base. The rubbing unit comprises a rubbing pad and its driving unit and is designed to rub the surface of the sample supported by the pedestal with the rubbing pad. An electrostatic voltage sensor for measuring the electrostatic voltage of the sample having been rubbed is provided on the measuring position. A data processor for processing the signal from the electrostatic voltage sensor is also provided.

The sample plate holding a sample is held by the sample table by being inserted into the sample table. With the back of the sample supported by the pedestal, the rubbing-sliding pad is allowed to slidably contact with the surface of the sample to perform rubbing for a specified time. Thereafter, the sample table is allowed to move to a measuring position to detect the electrostatic voltage of the sample by the electrostatic voltage sensor. The signal from the electrostatic voltage sensor is processed by the data processor.

This frictional electrostatic voltage measuring equipment performs rubbing and electrostatic voltage measurement almost without human power after a sample has been installed on the sample table, so that the electrostatic properties of the sample can be accurately and simply measured. The sample is held by the sample plate which in turn is inserted into the sample table. In the case of many samples to be measured, a plurality of sample plates holding respective samples can be prepared beforehand, and each sample plate may be sequentially inserted into the sample table to perform the measurement. Accordingly, an efficient measurement can be performed.

DETAILED DESCRIPTION OF THE PREFERRED EMBODIMENT

Figure 1:
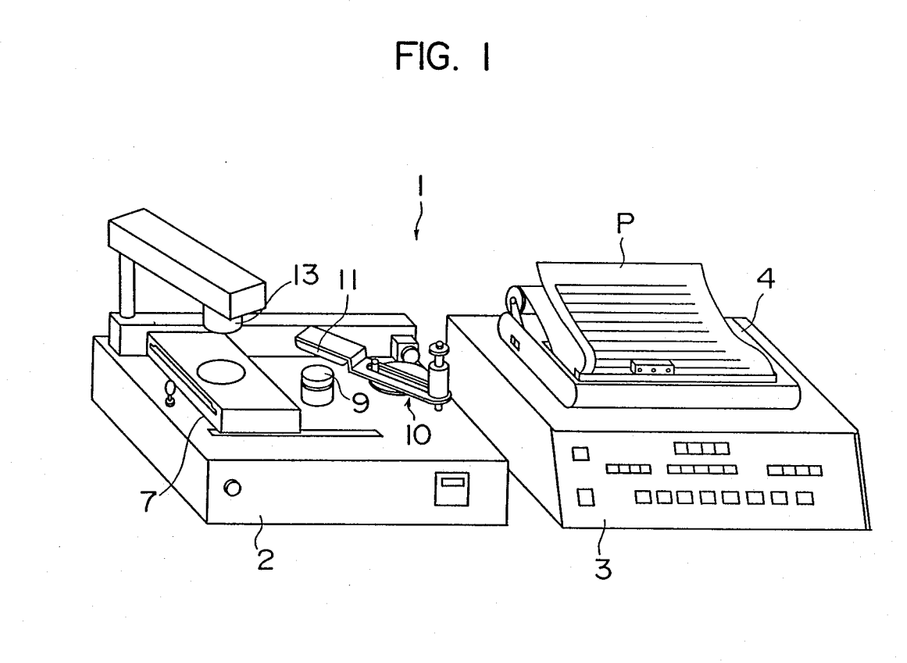
FIG. 1 is an overall perspective view of an embodiment of this invention.

FIG. 1 is a general configuration perspective view showing an embodiment of this invention in which this frictional electrostatic voltage measuring equipment 1 comprises a measuring unit 2 for applying friction to a sample and for measuring its electrostatic voltage, a data processor 3 for controlling the operation of the measuring unit 2 and for processing the data obtained, and a plotter 4.

Figure 2:
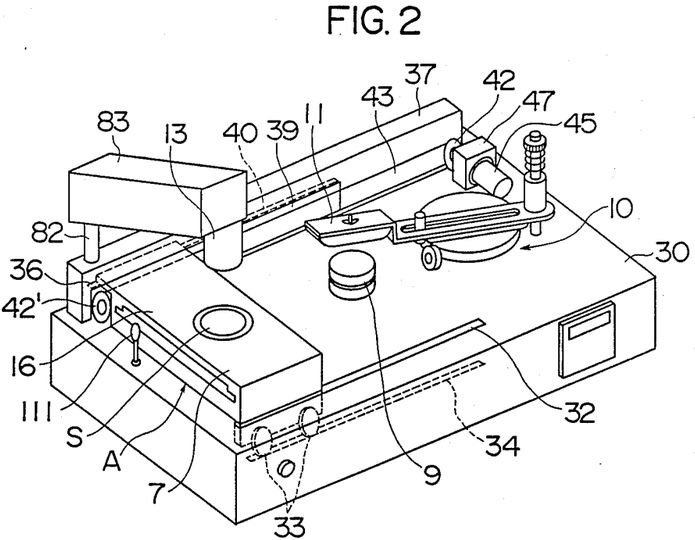
FIGS. 2 and 3 are perspective views of measuring equipment in different stages of operation.
Figure 3:
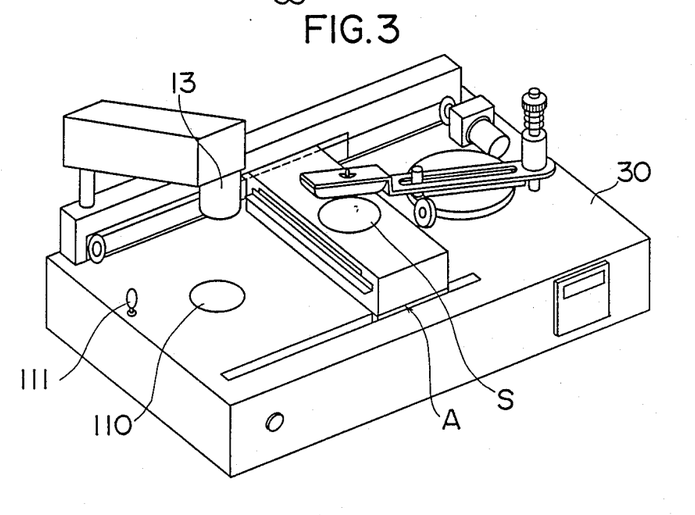

The measuring unit 2, as shown in FIGS. 2 and 3, is equipped with a sample holding section 7 for holding a sample S, a pedestal 9, a rubbing unit 10, and an electrostatic voltage sensor 13.

Figure 4:
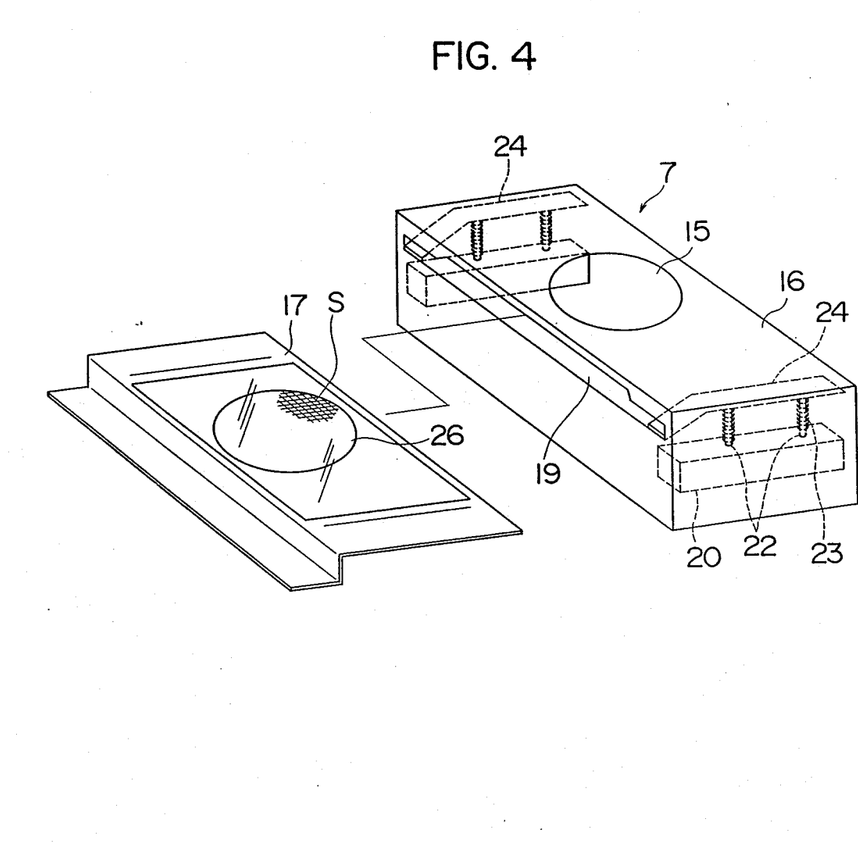
FIG. 4 is a perspective view of a sample holding portion.

The sample holding section 7, as shown in FIG. 4, is equipped with a slide-type sample table 16 whose top side is provided with a circular hole 15 to which the surface of the sample S is exposed, and a sample plate 17 for adherently fixing the sample S, the side of the sample table 16 having an opening of an insertion port 19 for inserting the sample plate 17. Also, the inside of the sample table 16 is provided with urging plates 24 and 24 each having legs 22 and 22 movable upward/downward to a base board and for urging the sample plate 17 against the back side of the top plate of the sample table 16 by the urging force of springs 23 and 23. The inlet side portion of the urging plates 24 and 24 inclines downward to front on said insertion port 19. A sample plate holding unit is comprised of these urging plate 24 and spring 23. A circular hole 26 is formed on the center portion of the staircase-form plate of the sample plate 17, and when the sample plate 17 is secured to the sample table 16, the hole 26 and the hole 15 on said table side just overlap each other. The sheet-form sample S is fixed to the top side of the sample plate 17 in stretched condition by fixing means such as pressure-sensitive tape. A sample with a low contraction and expansion properties such as woven goods and film can be measured even by allowing it to adhere directly to the sample plate with a tape without using the sample plate 17. Also, it is preferable that a sample with high contraction and expansion properties such as knit is fixed by a plurality of pins without using a pressure-sensitive tape and the like.

The edge on the near side of the sample table 16, as shown in FIG. 2, is integrally provided with a leg portion loosely engaged with a groove 32 provided on a case-form body base 30, and rollers 33 and 33 are installed on the leg portion. The roller 33 and 33 are so designed as to rotatably move on a rail 34 provided on a portion directly under the groove 32 when the table 16 is moved. Also, the edge on the far side of the sample table 16 is provided with a guide member 36 extending in the horizontal direction, so that the edge slides on a rail 40 within a groove 39 of a rising portion 37 provided on the body base 30.

Both edges of the front of the rising portion 37 are pivotably provided with pulleys 42 and 42' on which a wire 43 is installed. The wire 43 is locked to one edge of said sample table 16. One side pulley 42 is fixed to the rotating shaft of a pulse motor 45, and rotated by the normal/reverse revolution of the motor 45 so as to move the wire 43. When the wire 43 is moved, said sample table 16 is smoothly moved forward/backward between a measuring position A and a rubbing position B along the grooves 32 and 39. A rotary encoder 47 is installed on the motor 45 so as to detect the rotating amount of the motor 45. The motor 45 and the rotary encoder 47 for detecting the rotating amount of the motor 45 are connected to the data processor 3 (shown in FIG. 1) also serving as a controller.

Figure 5:
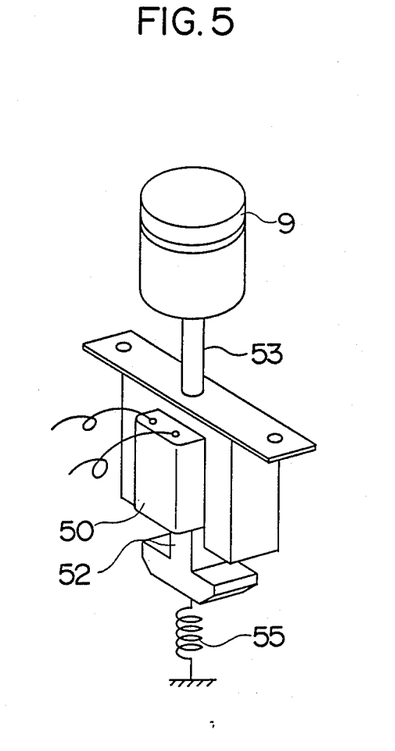
FIG. 5 is a schematic perspective view of a pedestal.

The pedestal 9, whose top side is of smooth wood face, is cylindrical in shape and supported by a rod 53 connected to a core 52 of a solenoid 50, as shown in FIG. 5. The core 52 is pulled downward by a spring 55 at all times and moved upward when the solenoid 50 is energized, so that the pedestal 9 is moved upward/downward according to that motion. The position of top side of the pedestal 9 is adjusted such that when the pedestal 9 is in a lowered position the top side is below the sample S set to the sample table 16, while when it is in a raised position due to energization of the solenoid 50 the top side is in contact with the back of the sample S. The solenoid 50 is also connected to the data processor 3.

Figure 6:
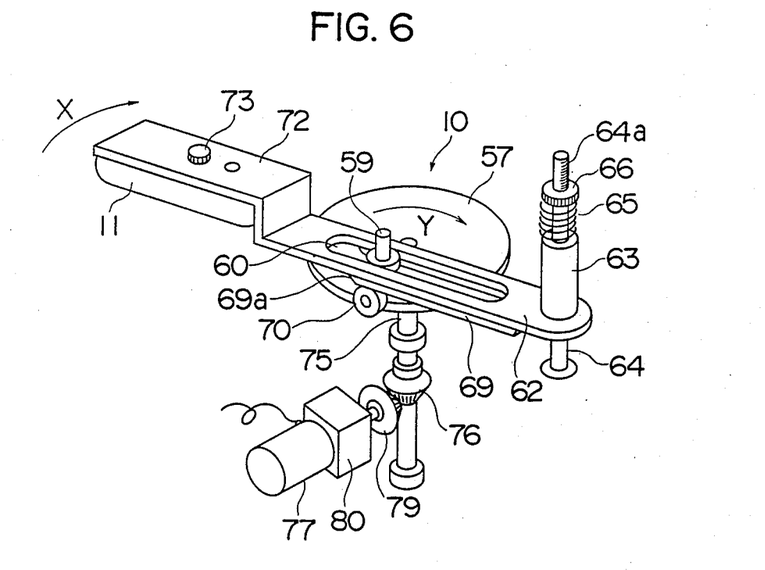
FIG. 6 is a schematic perspective view of a rubbing unit.

The rubbing unit 10, as shown in FIG. 6, is equipped with a crank mechanism in which a pin 59 is eccentrically provided on a turn table 57, and with a swing arm 62 having a slot 60 with which the pin of the crank mechanism is slidably engaged, the base portion of the swing arm 62 being provided integrally with a cylinder 63. The cylinder 63 is rotatably engaged with a supporting shaft 64, and the top end of the cylinder 63 is urged downward by a coil spring 65 externally engaged by the supporting shaft 64. The strength of the urging force of the coil spring 65 can be adjusted as appropriate by a nut 66 threadably attached to a thread portion 64a of the upper part of the supporting shaft 64.

The underside of the swing arm 62 is provided with a protrusion portion 69 whose end has an inclined face 69a, so that a roller 70 provided on the turn table 57 pushes upward the protrusion 69 at a specified position of the turn table 57. That is, the swing arm 62 swings by the crank mechanism along with the Y-arrow direction turning of the turn table 57, while said roller 70 comes off the protrusion portion 69 when the table moves in the X-arrow direction, so that the swing arm 62 is pushed downward by the coil spring 65. When the table moves in the counter X-arrow direction, the swing arm 62 is raised by the roller 70. When the swing arm 62 is raised, a rubbing-sliding pad 11 installed on the edge of the arm is raised from the sample surface, while when the swing arm 62 is lowered, said pad 11 comes in contact with the sample surface. Accordingly, the pad rubs the sample surface only when moved in the X-arrow direction, while the pad comes off the sample surface when moved back in the counter direction. Thus, rubbing is performed only when the pad moves in the one direction, so that there is little wrinkle or looseness developed even for thin material and knits. Accordingly, the distance from the sensor (when measuring) becomes constant, allowing a stable measuring accuracy to be obtained. The rubbing-sliding pad 11, having a blackboard eraser-form appearance, is constructed such that 5 to 10 grams of absorbent cotton is packed in a square holder, covered by a cleaning-treated cotton cloth or wool, and the covered holder is fixed with rubber band or pressure-sensitive tape. The pad 11 is installed on the step-form edge 72 of the swing arm 62 using a screw 73. Its attaching and detaching is easily performed.

A rotating shaft 75 of said turn table 57 is fixedly secured with bevel gear 76 with which a bevel gear 79 of a pulse motor 80 is engaged. The motor 80 is also installed with a rotary encoder 77, both of which are connected to the data processor 3 shown in FIG. 1.

Figure 7:
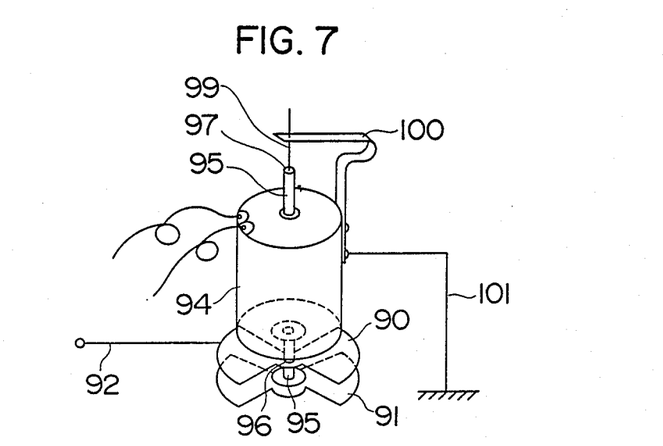
FIG. 7 is a perspective view of an electrostatic voltage sensor.

The electrostatic voltage sensor 13, as shown in FIGS. 1 and 2, is installed on the edge of a supporting case 83 so that when the sample table 16 is located on the measuring position A the sensor is located on just the position directly above the sample. The supporting case 83 is installed on a shaft 82 provided on the rising portion 37 of the body base 30. The electrostatic voltage sensor 13, being a rotary-sector type sensor, is provided with a sectorial electrostatic-induction detecting plate (sensor electrode) 90 and with a shielding plate 91 having the same form as that of the detecting plate both of which are spaced upward/downward of each other as shown in FIG. 7. The electrostatic induction detecting plate 90 located on the upper side is fixedly supported by an arm 92, while the shielding plate 91 located on the lower side is installed on a rotating shaft 95 of a brushless motor 94. The rotating shaft 95 of the motor 94 is non-contactedly inserted into a hole 96 which is bored in the center portion of the electrostatic-induction detecting plate 90. A conical pivot bearing section 97 is formed on the top end of the rotating shaft 95 of the motor 94, and an edge of a needle 99 formed of a conductor abuts on the pivot bearing section 97. The needle 99 is urged downward by a resilient plate 100 having conductivity, which is earthed through a lead wire 101. When the motor rotates in the condition that the sample S charged with static electricity is located on the position directly under the electrostatic voltage sensor 13, the shielding plate 91 is rotated, so that the detecting plate 90 with the same form as that of the shielding plate 91 when viewed from above is electrically induced or not depending upon the charged sample located on the under side. Accordingly, an electrostatic voltage is picked up as an alternate current corresponding to the magnitude of the voltage, and amplified by a preamplifier 121 shown in FIG. 8 so as to be supplied to the data processor 3.

For a bearing such as an antifriction bearing, oil film is formed on the surface of, for example, an anti-friction object (ball or roller) as the bearing shaft rotates, and through the oil film the antifriction object is rollingly moved. Accordingly, the shaft and the outside of the bearing become electrically and highly resistant, and the shielding plate 91 has a potential because the rotary shielding plate 91 is not completely earthed. Also, the high resistance of said shaft and outside of the bearing varies with the rotation of the shaft, with which the shaft potential varies, causing the electrostatic-induction detecting plate 90 to develop a noise. Although there is a possibility that measuring accuracy lowers due to this effect, in this equipment the rotating shaft 95 of the motor 94 is earthed through the needle 99, so that no measuring error due to said cause occurs.

The portion directly under the electrostatic voltage sensor 13, as shown in FIG. 3, is movably upward/downward provided with a disc-form electrode for calibration 110 with the same form as that of the hole 15 of the sample table 16. The electrode for calibration 110 is connected to a high-voltage power circuit for calibration 133 (FIG. 8) capable of applying a specified electrostatic voltage and is retracted to top side level of the body base 30 at all times; the electrode can be raised up to a specified height close to the electrostatic voltage sensor 13 by operating an electrode lifting lever 111. The electrode for calibration 110 allows the sensitiveness of the electrostatic voltage sensor 13 to be calibrated.

Figure 8:
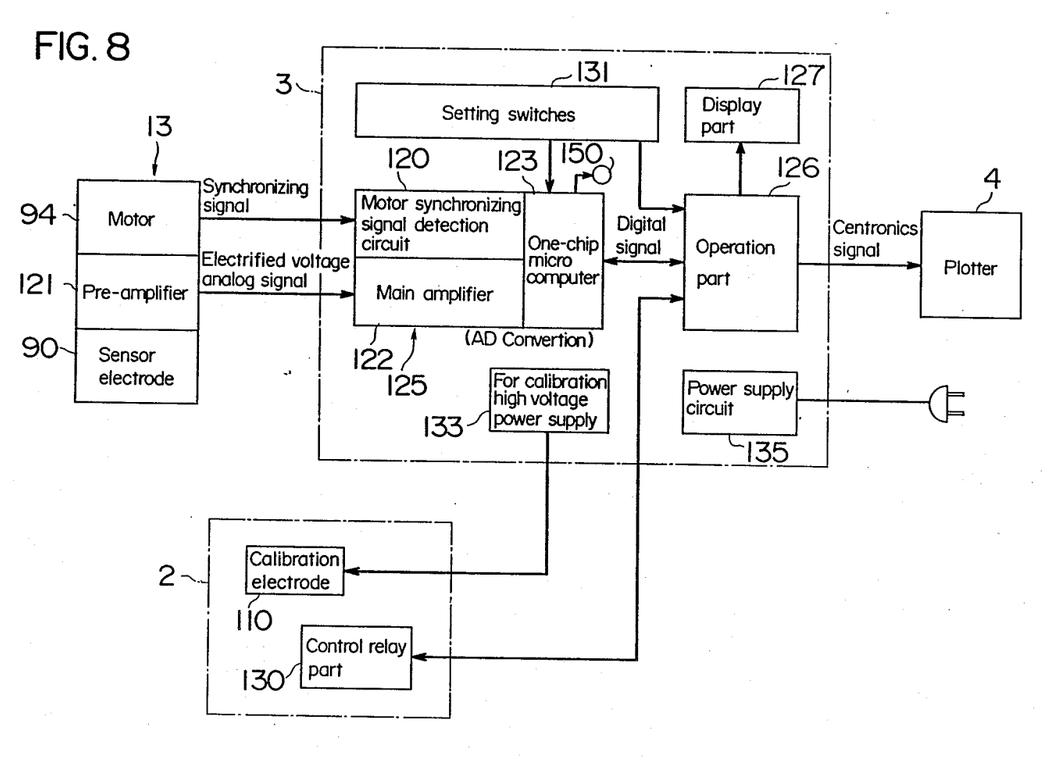
FIG. 8 is a block diagram showing the general configuration.

The data processor 3 is configured as shown in FIG. 8. That is, both the synchronizing signal from the motor 94 of the electrostatic voltage sensor 13 and the electrostatic voltage analog signal from a preamplifier 121 are supplied to an A/D converter 125 including a motor synchronizing signal detecting circuit 120, a main amplifier 122 and a one-chip microcomputer; the digital signal from the A/D converter 125 is supplied to an arithmetic section (computer) 126. In the arithmetic section 126, the arithmetic operation of measured data is performed, and the results are supplied to a display section 127 and to the plotter 4.

Also, to the arithmetic section 126 a control relay section 130 for driving the motor 45, the solenoid 50 and the motor 80 of the measuring unit 2, and a switch group for setting 131 are connected, so that the control of the entire equipment operation as well as the setting of measuring conditions are performed. Further, the electrode for calibration 110, as previously mentioned, is connected with the high-voltage power for calibration 133. In the figure, 135 is a power circuit connected to the power of 100V AC and for obtaining a direct current voltage.

Figure 9:
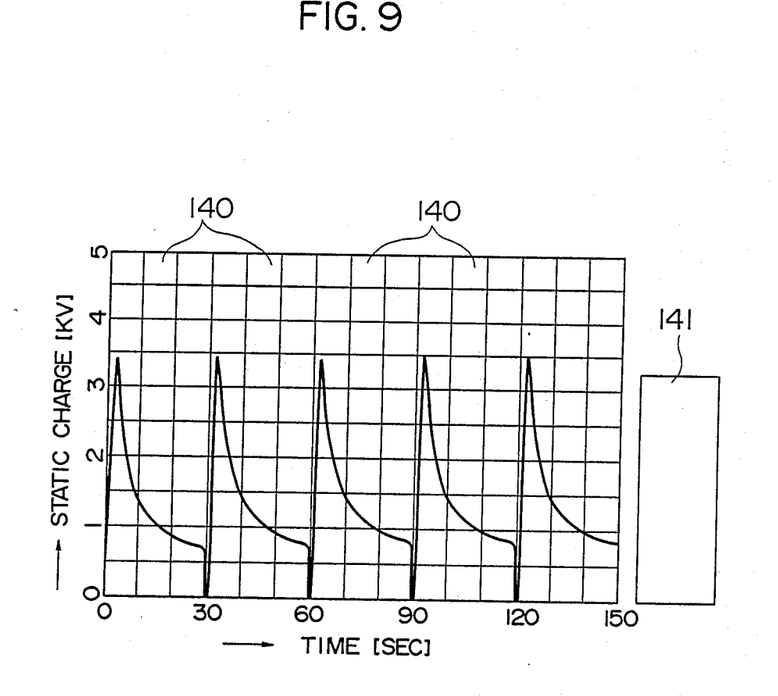
FIG. 9 is a schematic view of a recorded contents by a plotter.

The plotter 4, as shown in FIG. 9, records a time-dependent change in electrostatic voltage of the sample with a graph, and also records a peak voltage in one measurement on a recording position 140 above each graph, for example, such as −3.42 KV. In the figure, the axis of ordinate indicates electrostatic voltage and the axis of abscissa does time (second or minute). The coordinate scale is also arranged to be drawn as a chart on a recording paper P by the plotter 4 according to a set condition. After a preset number of measurements (for example, five measurements) has been performed per one sample, statistically processed results will be also recorded on a column 141 on the right side of the chart with respect to the average and degree of variability of peak value, the average and degree of variability of electrostatic voltage after the first set time (for example, 10 seconds) has lapsed from the initiation of measurement, the average and degree of variability of electrostatic voltage after the second set time (for example, 30 seconds) has lapsed, if necessary the average and degree of variability of further electrostatic voltage after the nth set time has elapsed, and the average and degree of variability of the half-life of electrostatic voltage. Thus, the measured data is statistically processed and at the same time is displayed, thereby providing a practically very convenient means.

The recording of each measured data by the plotter 4 is performed by sampling the data for each specified time and by plotting them on the recording paper. However, the electrostatic voltage immediately after the initiation of recording varies very rapidly as shown in FIG. 9, for a specified time (for example, 10 seconds) from the initiation, so that the sampling interval of the plotter is made shorter than that for the subsequent time (for example, ¼). This allows a rapid change of data to be sufficiently adapted, and a high accuracy graph to be drawn.

Figure 10:
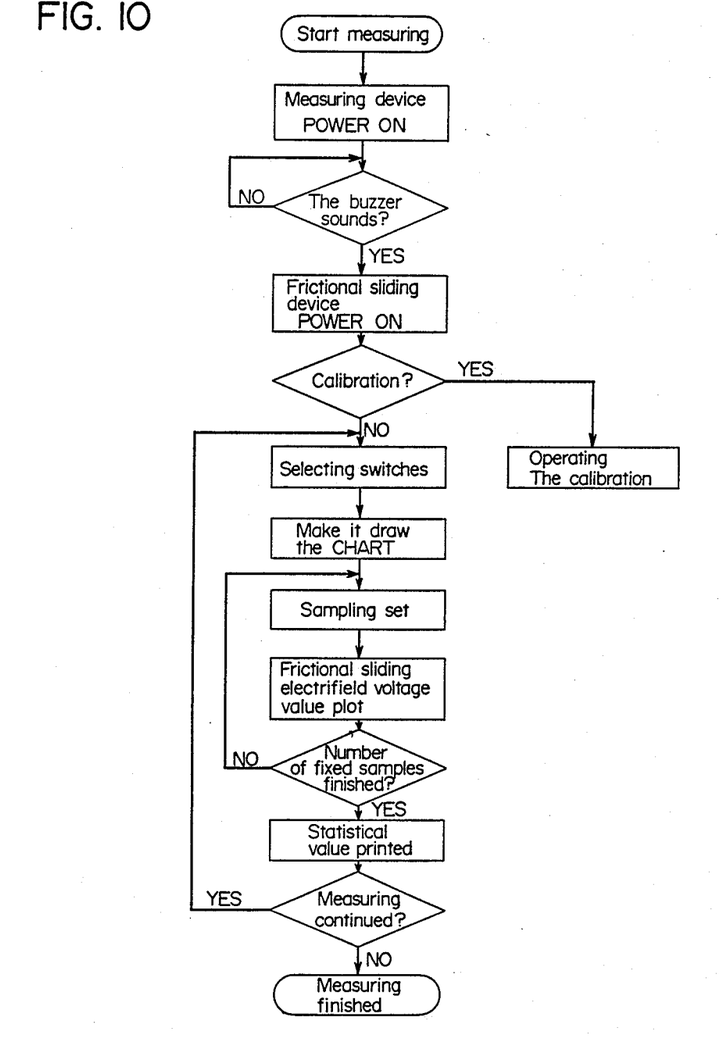
FIG. 10 is a flowchart of operation.

Then, referring to the flowchart of FIG. 10 showing a measuring operation, the method of application of the frictional electrostatic voltage measuring equipment 1 is illustrated hereinafter.

First, place a sample cut in nearly a square on the sample plate 17 so as to cover the hole 26, and adherently fix the sample with a pressure-sensitive tape. At this time, fix the sample to develop no wrinkles on its surface. Insert the sample plate 17 installed with the sample into the insertion port 19 of the sample table 16, and fully press into the port so that both the holes 15 and 26 are overlapped with each other.

After the power of the measuring unit 2 has been confirmed to be off, turn on the power for the data processor 3 and the plotter 4, and wait to perform subsequent operation until a buzzer 150 sounds. Since the buzzer notifies that the preparation of the plotter 4 has been completed, when it sounds turn on the switch of the measuring unit 2. Thereafter, selectively set each switch of the switch group for setting, for example, a switch for setting the voltage range, a switch for setting the number of measurements, and a switch for setting the measuring time. Although, when performing calibration, a calibration switch should be operated to allow the calibrating operation mentioned below to perform, usually the calibration is not required.

After the above settings have been performed, allow the plotter 4 to draw the chart scale for X axis and Y axis on the recording paper P. When switching on the measuring unit 2 having set the sample S, the sample table 16 moves to the rubbing position B, the pedestal 9 rises to support the underside of the sample, and the slidable rubbing in only one direction is performed by a specified number of rubbings (for example, 12 rubbings) with the rubbing-sliding pad 11 of the rubbing unit 10. After the rubbing has finished, the pedestal 9 lowers, and the sample table 16 returns back to the measuring position A so that the electrostatic voltage of the sample is detected by the electrostatic voltage sensor 13. The detecting signal is processed by the data processor 3, and recorded by the plotter 4. After the operation has been performed by a set number of operations (for example, five operations), the statistical values obtained are printed. After a specified number of measurements for one sample have been finished, perform the similar measurement for another sample.

Then, the method of calibration of the electrostatic voltage sensor 13 is described hereinafter. First, remove the sample plate 17 from the sample table 16 located on the measuring position A, and raise the electrode for calibration 110 up to the position of the hole 15 by pulling up the lever 111. In this condition, apply a specified calibration voltage (for example, 15 KV) to the electrode for calibration 110 to perform the detection by the electrostatic voltage sensor 13. Although the detected results are recorded by the plotter 4, when the value is outside of a set voltage, calibrate the value by performing sensitiveness adjustment.

Although in said embodiment a rotary sector type sensor for the electrostatic voltage sensor 13 is used, a vibrating-read type, or a mechanical or electrical chopper type sensor may be used.

What is claimed is:

1. Frictional electrostatic voltage measuring equipment comprising:
   a body base;
   a sample table installed on said body base so as to be reciprocally moveable between a measuring position and a rubbing position, said sample table having a top plate with a hole for exposing said sample and a sample plate holding unit for holding the sample plate by resiliently urging the plate against the back of said top plate;
   a sample plate detachably inserted into said sample table for holding a sheet-form sample in stretched condition;
   a pedestal at said rubbing position of said body base for supporting said sample from its back;
   a rubbing unit comprising a rubbing pad and a driving unit for rubbing the surface of said sample supported by said pedestal;
   an electrostatic voltage sensor provided at said measuring position for detecting the electrostatic voltage of the sample having been rubbed; and
   a data processor for processing the signal from said electrostatic voltage sensor.

2. Frictional electrostatic voltage measuring equipment as in claim 1, wherein said pedestal is mounted so as to be movable upwardly and downwardly to support the back of the sample by moving upward when rubbing.

3. Frictional electrostatic voltage measuring equipment as in claim 1, wherein said driving unit of said rubbing pad allows the rubbing pad to be rotatable in a specified track and to be slidably in contact with the surface of the sample in one direction.

4. Frictional electrostatic voltage measuring equipment as in claim 1, wherein said data processor is provided with arithmetic operation means for statistically processing the results of a plurality of measurements and for displaying them.

5. Frictional electrostatic voltage measuring equipment comprising:
   a body base;
   a sample table installed on said body base so as to be reciprocally movable between a measuring position and a rubbing position;
   a sample plate detachably inserted into said sample table for holding a sheet-form sample in stretched condition;
   a pedestal at said rubbing position of said body base for supporting said sample from its back;
   a rubbing unit comprising a rubbing pad and a driving unit for rubbing the surface of said sample supported by said pedestal;
   an electrostatic voltage sensor provided at said measuring position for detecting the electrostatic voltage of the sample having been rubbed; a calibration electrode for calibrating the sensitiveness of said electrostatic voltage sensor; and
   a data processor for processing the signal from said electrostatic voltage sensor.

6. Frictional electrostatic voltage measuring equipment comprising:
   a body base;
   a sample table installed on said body base so as to be reciprocally moveable between a measuring position and a rubbing position;
   a sample plate detachably inserted into said sample table for holding a sheet-form sample in stretched condition;
   a pedestal at said rubbing position of said body base for supporting said sample from its back;
   a rubbing unit comprising a rubbing pad and a driving unit for rubbing the surface of said sample supported by said pedestal;
   an electrostatic voltage sensor provided at said measuring position for detecting the electrostatic voltage of the sample having been rubbed wherein said electrostatic voltage sensor is of the rotatably driven rotary sector type and has a detecting plate wherein said detecting plate has a sample side and a processing side and a shielding plate which is located on the sample side rather than on the processing side; and a data processor for processing the signal from said electrostatic voltage sensor.

7. Frictional electrostatic voltage measuring equipment as in claim 6 including a conductive needle positioned with its edge in contact with the end face of the rotating shaft of the motor driving the shielding plate of said electrostatic voltage sensor, and a conductive resilient plate for urging the needle against said rotating shaft, the resilient plate being connected to an earth means.

* * * * *